United States Patent [19]
Chantler et al.

[11] Patent Number: 6,103,681
[45] Date of Patent: Aug. 15, 2000

[54] LAVATORY CLEANSING COMPOSITIONS

[75] Inventors: Stephen John Chantler, Lympne; Paul Henry Dobson, Wilmslow, both of United Kingdom

[73] Assignee: Quest International B.V., Naarden, Netherlands

[21] Appl. No.: 09/180,542

[22] PCT Filed: May 9, 1997

[86] PCT No.: PCT/GB97/01257

§ 371 Date: Jun. 4, 1999

§ 102(e) Date: Jun. 4, 1999

[87] PCT Pub. No.: WO97/43397

PCT Pub. Date: Nov. 20, 1997

[30] Foreign Application Priority Data

May 11, 1996 [GB] United Kingdom .................. 9609865

[51] Int. Cl.$^7$ ................................ C11D 3/50; C11D 17/00
[52] U.S. Cl. .................... 510/191; 510/192; 510/102; 510/446; 510/447; 510/495; 424/76.7; 4/224; 134/42
[58] Field of Search ...................... 510/191, 192, 510/102, 446, 447, 495; 424/76.7; 4/224; 134/42

[56] References Cited

U.S. PATENT DOCUMENTS

| | | | |
|---|---|---|---|
| 4,218,432 | 8/1980 | Watanabe et al. | 424/14 |
| 4,396,522 | 8/1983 | Callicott et al. | 252/163 |
| 4,578,207 | 3/1986 | Holdt et al. | 252/134 |
| 4,604,487 | 8/1986 | Wiegers et al. | 568/715 |
| 4,666,671 | 5/1987 | Purzycki et al. | 422/5 |
| 4,842,853 | 6/1989 | Gebauer et al. | 424/76.1 |
| 4,994,266 | 2/1991 | Wells | 424/76.7 |
| 5,543,439 | 8/1996 | McDermott et al. | 523/102 |

*Primary Examiner*—Lorna M. Douyon
*Attorney, Agent, or Firm*—Pillsbury Madison & Sutro LLP

[57] ABSTRACT

A solid lavatory cleansing composition comprises phenyl ethyl alcohol of at least 2.5% by weight which acts as a fragrance and also as an antibacterial agent.

10 Claims, No Drawings

LAVATORY CLEANSING COMPOSITIONS

FIELD OF THE INVENTION

This invention relates to lavatory cleansing compositions and particularly concerns solid lavatory cleansing compositions either intended to be positioned in a toilet bowl or urinal in such a manner that the composition is rinsed with water on flushing (toilet rim blocks or toilet rinse blocks) or intended to be positioned in a toilet or urinal cistern, immersed in flush water (in-cistern blocks).

BACKGROUND TO THE INVENTION

Solid lavatory cleansing compositions are well known. See, for example, EP0167210, EP0350227, EP0462643, EP0526437, WO95/25162 and U.S. Pat. No. 4,666,671, for a discussion of solid compositions intended for use in toilet bowls, ie toilet rim blocks or toilet rinse blocks. GB 2290300 discloses toilet rim blocks comprising polyvinyl alcohol or partially hydrolysed polyvinyl acetate with fragrance material that may include a small amount of beta phenyl ethyl alcohol, at a level of 0.47% by weight.

SUMMARY OF THE INVENTION

According to the present invention there is provided a solid lavatory cleansing composition comprising phenyl ethyl alcohol (PEA) in an amount of at least 2.5% by weight of the total weight of the composition.

PEA is a known fragrance material and acts to impart desirable fragrance properties to the composition. PEA also has antibacterial properties, so this material also acts to impart antibacterial properties to the composition.

The composition may be otherwise of generally conventional formulation.

The composition desirably comprises surfactant, preferably anionic surfactant, for cleaning purposes. Surfactant is suitably present in an amount in the range 25 to 75% by weight, conveniently 25 to 50% by weight, preferably 30 to 40% by weight of the total weight of the composition.

Anionic surfactants which can be used in the present invention include for example the alkali metal alkyl substituted benzene sulphonates, alkali metal long chain alkyl sulphates, alkali metal ether sulphates derived from long chain alcohols and alkyl phenols, alkali metal alkane sulphonates, alkali metal olefin sulphonates and alkali metal sulphosuccinates, of which the sodium salts are preferably used.

Preferred anionic surfactants are sodium $C_9$–$C_{14}$ alkyl benzene sulphonates, sodium $C_{11}$–$C_{10}$ olefin sulphonates, sodium $C_{11}$–$C_{20}$ alkane sulphonates and sodium long chain $C_{10}$–$C_{14}$ alkyl sulphates or mixtures thereof, sodium alkyl benzene sulphonates being particularly preferred as the main surfactant component.

In addition, other types of surfactants, such as nonionic surfactants including ethoxylated nonionic compounds, fatty acid alkanolamides and amine oxides, may be incorporated as desired, but only in amounts not exceeding 20% by weight, preferably less than 10% by weight, since they could otherwise tend to affect the foaming properties and rate of wear of the composition.

The composition desirably also includes a filler, which is suitably present in an amount in the range 20 to 75% by weight, preferably 40 to 65 % by weight, more preferably 50 to 60% by weight of the total weight of the composition.

The filler can be an electrolyte, such as sodium sulphate, sodium chloride, sodium carbonate and phosphates, such as sodium triphosphate, hexametaphosphate, pyrophosphate and orthophosphate; or and inert material, such as calcite, clay and urea. A mixture of filler materials may be used.

Fragrance, comprising PEA possibly in combination with other fragrance materials, is typically present in an amount in the range 5 to 20% by weight, eg about 10% of the total weight of the composition. The fragrance preferably comprises at least 50% by weight of the weight of the fragrance, corresponding to PEA levels in the composition of at least 2.5% to at least 10% by weight of the total weight of the composition.

The composition may additionally include a solubility control agent to reduce solubility of the composition and so extend the life of the composition in use.

Suitably solubility control agents include natural polysaccharide gums such as guar gum, xanthan gum, tragacanth, carragheenan, etc and their semi-synthetic analogues as produced by fermentation.

Other solubility control agents may additionally or alternatively be used, including waxes, such as waxes of natural origin, polyethylene waxes an amide waxes; long chain (eg. containing more than 10 carbon atoms) fatty alcohols such as stearyl or behenyl alcohol; long chain, (eg. containing more than 10 carbon atoms) fatty acids, such as stearic acid, and their salts; esters of long chain fatty alcohols with aliphatic carboxylic acids, such as stearyl acetate; esters of long chain fatty acids with mono or polyhydric alcohols, such as ethyl stearate or glycerol tristerate or mono-, di- or tri-glycerides of natural origin; fatty acid mono- or di-alkanolamides, such as coconut monoethanolamide; ethoxylated products of fatty acid mono- or di-ethanolamides containing low amounts, eg. 2 to 4 units, of ethylene oxide per mole; paradichlorobenzene; or long chain aliphatic hydrocarbons of natural of synthetic origin.

Preferred solubility control agents are generally insoluble fragrance materials, particularly pine oil, which function both as fragrances and solubility control agents.

Solubility control agent, if present, is suitably used in an amount in the range 1 to 10% by weight, preferably 2 to 5% by weight of the total weight of the composition. Suitable levels depending on factors including composition ingredients and intended block life, and can be readily determined by experiment.

Use of solubility control agent such as pine oil may enable PEA to be used at lower levels than would otherwise be the case without compromising performance.

The composition may optionally also contain non-surfactant nonionic polymeric materials, such as polyethylene glycols and minor ingredients, such as dyes, germicides, fungicides, bleaches, opacifiers and the like as desired. For example, in-cistern products typically include dye to colour the flush water, but this is not essential.

The composition is conveniently in the form of a block, which suitably has a weight in the range 20 to 150 grams, preferably in the range 50 to 80 grams. The block may be of any suitable desired shape and size for positioning in a toilet bowl or urinal for a rim block or for location in a cistern for an in-cistern block.

The composition may be conveniently formed into blocks by mixing the ingredients to form a dough, extruding the dough and cutting the extruded dough, eg as described in EP 0167210.

For a rim block, the composition is typically placed in or on a suitable container of holder designed to be suspended from the rim of a toilet bowl or urinal, to hang within the bowl or urinal just below the rim in a position for the composition to be rinsed with flush water on flushing of the toilet. The container or holder is conveniently of plastics material and usually has apertured walls to enable flush water to contact and flow past the composition.

In a further aspect, the invention provides a container or holder having located therein or thereon a solid lavatory cleansing composition in accordance with the invention. An in-cistern block is used by simply being placed in a cistern immersed in the cistern water. No container or holder is used, although for handling/aesthetic purposes the block is usually wrapped in water-soluble film.

The invention will be further described, by way of illustration, in the following Examples.

EXAMPLE 1

A solid lavatory cleansing composition intended for use as a rim block has the following formulation.

|  | % w/w |
| --- | --- |
| Sodium dodecylbenzene sulphonate | 35 |
| Fragrance (50% PEA) | 10 |
| Water | 0.5 |
| Sodium Sulphate (filler) | 54.5 |

The ingredients are mixed to form a dough which is extruded and cut into lengths to form blocks having a weight of about 50 grams, as described in EP 0167210.

The blocks are located in apertured plastics holders and in use are hung from the rim of a toilet bowl to be rinsed by flush water on flushing.

The blocks have good cleansing properties, with the PEA acting as a fragrance and also as an antibacterial agent.

EXAMPLE 2

A solid lavatory cleansing composition intended for use as an in-cistern product was made by the method described in Example 1. The composition has the following formulation:

|  | % w/w |
| --- | --- |
| Sodium dodecylbenzene sulphonate | 40.0 |
| Sodium sulphate (filler) | to 100 |
| Fragrance (50% PEA) | 6.0 |
| Water | 0.5 |
| Dye - Acid Blue 9 | 4.0 |

Blocks of the composition of desired size and shape are wrapped in water-soluble film. In use, a wrapped block is located in a toilet cistern, immersed in the cistern water.

The blocks have good cleansing properties, with PEA acting as a fragrance and also as an antibacterial agent.

EXAMPLE 3

A series of blocks of lavatory cleansing compositions were prepared as described in Example 1, but incorporating varying amounts of fragrance (50% PEA) and hence varying amounts of PEA.

The germ kill efficacy of the blocks and also a number of commercially available bleach- containing lavatory cleansing compositions was then tested.

The test protocol was as follows:
Standard Dirty Water (S.D.W.)
Containing approximately $10^4$ cfu/mL
Prepared from:

| 1. Synthetic hard water of 200 ± 10 mg/Kg hardness | 18 parts |
| --- | --- |
| 2. Horse serum (Oxoid, sterile) | 2 parts |
| 3. *E. coli* NCIB 9132 grown in Nutrient broth (Oxoid), diluted after 24 hrs growth with sterile distilled water to give approx. $10^5$ cfu/mL | 1 part |

SAMPLES

Samples were dissolved in sterile distilled water, to give solutions of appropriate concentration corresponding with a block life of 500 flushes, each of 9L.

Test Procedure

At time zero, 1 mL of S.D.W. (containing approximately 10,000 cfu) was added to 9 mL of sample solution and after 2, 5, 10, 30, 60 and 120 minutes survivors were counted using pour plates and incubation @ 37±1° C. for 24 hours.

A blank test was also performed, using sterile distilled water in place of sample solution, to determine the number of cfu/mL added to the sample solutions.

Results were as follows:

| | Test Block 1 (0% PEA) | | |
| --- | --- | --- | --- |
| Survivors after | 2 minutes | 9400 | 6% kill |
| | 5 minutes | 10000 | 0% kill |
| | 10 minutes | 9400 | 6% kill |
| | 30 minutes | 7200 | 28% kill |
| | 60 minutes | 6400 | 36% kill |
| | 120 minutes | 3200 | 68% kill |
| | Test Block 2 (3.60% PEA) | | |
| Survivors after | 2 minutes | 330 | 96.7% kill |
| | 5 minutes | 330 | 96.7% kill |
| | 10 minutes | 300 | 97% kill |
| | 30 minutes | 270 | 97.3% kill |
| | 60 minutes | 240 | 97.6% kill |
| | 120 minutes | 170 | 98.3% kill |
| | Test Block 3 (5.76% PEA) | | |
| Survivors after | 2 minutes | 660 | 93.4% kill |
| | 5 minutes | 660 | 93.4% kill |
| | 10 minutes | 660 | 93.4% kill |
| | 30 minutes | 440 | 95.6% kill |
| | 60 minutes | 440 | 95.6% kill |
| | 120 minutes | 220 | 97.8% kill |
| | Test Block 4 (12.69% PEA) | | |
| Survivors after | 2 minutes | 1200 | 88% kill |
| | 5 minutes | 660 | 93.4% kill |
| | 10 minutes | 660 | 93.4% kill |
| | 30 minutes | 440 | 95.6% kill |
| | 60 minutes | 440 | 95.6% kill |
| | 120 minutes | 220 | 97.8% kill |
| | Test Block 5 (19.16% PEA) | | |
| Survivors after | 2 minutes | 440 | 95.6% kill |
| | 5 minutes | 440 | 95.6% kill |
| | 10 minutes | 440 | 95.6% kill |
| | 30 minutes | 1000 | 90% kill |
| | 60 minutes | 660 | 93.4% kill |
| | 120 minutes | 440 | 95.6% kill |
| | S. C. Johnson Bleach Power Rim Stick | | |
| Survivors after | 2 minutes | 4400 | 56% kill |

-continued

|  | | | |
|---|---|---|---|
|  | 5 minutes | 660 | 93.4% kill |
|  | 10 minutes | 440 | 95.6% kill |
|  | 30 minutes | 440 | 95.6% kill |
|  | 60 minutes | 440 | 95.6% kill |
|  | 120 minutes | 440 | 95.6% kill |
|  | Jeyes Parazone Rim Stick | | |
| Survivors after | 2 minutes | 390 | 96.1% kill |
|  | 5 minutes | 260 | 97.4% kill |
|  | 10 minutes | 130 | 98.7% kill |
|  | 30 minutes | 50 | 99.5% kill |
|  | 60 minutes | 50 | 99.5% kill |
|  | 120 minutes | 10 | 99.9% kill |
|  | Domestos Rim Stick | | |
| Survivors after | 2 minutes | 180 | 98.2% kill |
|  | 5 minutes | 120 | 98.8% kill |
|  | 10 minutes | 50 | 99.5% kill |
|  | 30 minutes | 70 | 99.3% kill |
|  | 60 minutes | 40 | 99.6% kill |
|  | 120 minutes | 20 | 99.8% kill |

What is claimed is:

1. A solid lavatory cleansing composition consisting essentially of, by weight of the total composition:
   from 25 to 75% by weight of surfactant:
   from 50 to 75% by weight of filler:
   from 1 to 10% by weight of solubility control agent; and
   from 5 to 20% by weight of fragrance comprising phenyl ethyl alcohol optionally in combination with other fragrance materials, wherein said phenyl ethyl alcohol is present in an amount of at least 2.5% by weight of the total weight of the composition, said amount being sufficient to provide both fragrance and an effective antibacterial activity.

2. A composition according to claim 1, wherein the surfactant is anionic.

3. A composition according to claim 2, wherein the surfactant is sodium dodecylbenzene sulphonate.

4. A composition according to claim 3, wherein the surfactant is present in an amount in the range 25 to 50% by weight of the total weight of the composition.

5. A composition according to claim wherein the surfactant is present in an amount of 30 to 40% by weight of the composition.

6. A composition according to claim 1, wherein the filler is sodium sulphate.

7. A composition according to claim 1, wherein the fragrance comprises at least 50% by weight phenyl ethyl alcohol based on the total weight of the fragrance.

8. A composition according to claim 1 wherein the solubility control agent is pine oil.

9. A composition according to claim 1, in the form of a block.

10. In a method of cleansing a toilet bowl or urinal by positioning a solid lavatory cleansing composition in the bowl or urinal for contact with flush water, the improvement wherein the solid lavatory composition is according to the composition of claim 1.

* * * * *